US006800072B2

(12) United States Patent
Patzer

(10) Patent No.: US 6,800,072 B2
(45) Date of Patent: Oct. 5, 2004

(54) CONTRAST DISPENSING SYSTEM

(75) Inventor: Charles R. Patzer, Columbus, OH (US)

(73) Assignee: Medex, Inc., Carlsbed, CA (US)

(*) Notice: Subject to any disclaimer, the term of this patent is extended or adjusted under 35 U.S.C. 154(b) by 113 days.

(21) Appl. No.: 10/180,730

(22) Filed: Jun. 26, 2002

(65) Prior Publication Data

US 2004/0002685 A1 Jan. 1, 2004

(51) Int. Cl.[7] .................... A61M 5/00; A61M 37/00; A61B 19/00; B67D 5/58; B65D 51/16
(52) U.S. Cl. .................... 604/260; 604/83; 604/247; 604/251; 604/254; 604/411; 222/189.09; 215/308; 215/311; 215/DIG. 3; 220/254.3; 220/374
(58) Field of Search ................. 604/48, 80, 82, 604/83, 85, 93.01, 246, 247, 248, 250, 251, 252, 254, 255, 256, 257, 260, 262, 6.15, 6.16, 407, 411, 414, 415, 416; 222/189.09, 481.5; 215/308, 311, DIG. 3; 220/254.3, 374

(56) References Cited

U.S. PATENT DOCUMENTS

| | | |
|---|---|---|
| 3,881,640 A | 5/1975 | Noble |
| 3,976,068 A | 8/1976 | Lundquist |
| 4,078,563 A | 3/1978 | Tuseth |
| 4,175,558 A | 11/1979 | Hess, III et al. |
| 4,317,473 A | 3/1982 | Gaydos |
| 4,332,247 A | 6/1982 | Mittleman et al. |
| 4,552,288 A | * 11/1985 | Flider .................... 222/482 |
| 4,553,964 A | 11/1985 | Sasaki |
| 4,673,397 A | 6/1987 | Lynn et al. |
| 4,694,838 A | 9/1987 | Wijayarthna et al. |
| 4,734,091 A | 3/1988 | Boyle et al. |
| 5,059,173 A | 10/1991 | Sacco |
| 5,328,463 A | 7/1994 | Barton et al. |
| 5,334,170 A | 8/1994 | Moroski |
| 5,356,375 A | 10/1994 | Higley |
| 5,423,346 A | 6/1995 | Daoud |
| 5,423,751 A | 6/1995 | Harrison et al. |
| 5,443,453 A | 8/1995 | Walker et al. |
| 5,533,978 A | 7/1996 | Teirstein |
| 5,569,208 A | 10/1996 | Woelpper et al. |
| 5,575,779 A | 11/1996 | Barry |
| 5,593,385 A | 1/1997 | Harrison et al. |
| 5,697,904 A | 12/1997 | Raines et al. |
| 6,073,812 A | * 6/2000 | Wade et al. ........... 222/189.09 |
| 6,106,504 A | * 8/2000 | Urrutia ..................... 604/251 |

FOREIGN PATENT DOCUMENTS

WO    WO 93/20863 A    10/1993

OTHER PUBLICATIONS

Photograph of Medex–designed narrow flex chamber CCD.
The Medex Contrast Control Device (2 pp) (10/98).
"Cost–Effective CCD Features Unique Design" (1 page) *MEEN/MIMS Magazine*, p. 16 (Oct. 1999).
Diagnostic/Interventional (CMS Series), B. Braun, (2 pp).
Photograph of Medex–designed long burette CCD.
Partial International Search Report dated Oct. 10, 2003 (Annex to Form PCT/ISA/206) (2 pages).

* cited by examiner

*Primary Examiner*—Brian L. Casler
*Assistant Examiner*—Mark K. Han
(74) *Attorney, Agent, or Firm*—Wood, Herron & Evans, LLP

(57) ABSTRACT

A contrast dispensing system (10) reduces cost by directly connecting a check valve (210) to and between the reservoir inlet port (220) and the mating luer connector (204) of a disposable set (200). A contrast dispensing system (10) includes as part of the reservoir (212) an integrally molded cap (280) having the inlet port (200) and a lateral pipe (300) to confine contrast media (14) therein and disperse it at separate locations (334, 336) within the chamber (260) of reservoir (212). The reservoir (212) may have a vent port (284) with a flip cap (294) for selectively opening or closing same.

43 Claims, 3 Drawing Sheets

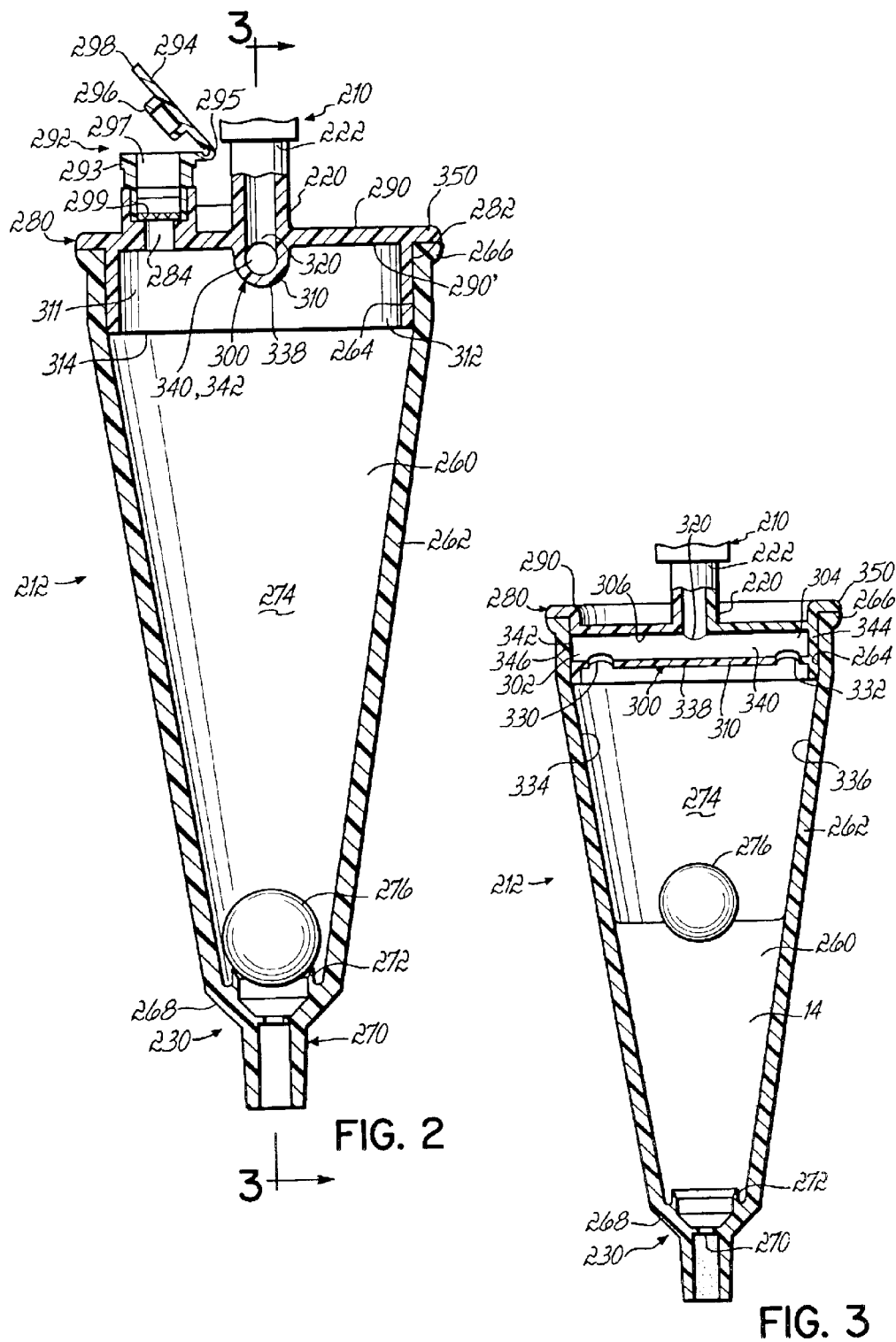

CONTRAST DISPENSING SYSTEM

BACKGROUND OF THE INVENTION

I. Field of the Invention

The present invention relates to contrast dispensing systems.

II. Description of Prior Art

Contrast dispensing systems are well known and provide a mechanism for selectively coupling a source of contrast media, such as from a pressurized bag or bottle, to a patient through a manifold and syringe structure. Contrast dispensing systems typically have a spike at one end designed to selectively engage the contrast media source and an outlet luer connector at the other end adapted to attach to one port of the manifold. Another port of the manifold is connected to a syringe. The syringe and manifold may be manipulated to pull contrast media into the syringe, and then to expel same back out to the patient through yet another port of the manifold.

The media is usually supplied in bulk volume far in excess of that needed for one patient's purposes. To reduce waste, many contrast dispensing systems include a reservoir between the spike and the luer connector to temporarily hold a quantity of the contrast media. A quantity of the contrast media may be loaded into tile reservoir from the source. The media is then taken from tile reservoir by manipulation of the manifold and syringe to dispense the contrast media to the patient. Thereafter, part or all of the contrast dispensing system may be disposed of and a new system put in place for the next patient so as not to waste the remaining contrast media in the bag or bottle. In an effort to avoid cross-contamination between patients, many such systems include a reusable set carrying the spike, a disposable set carrying the outlet luer connector, a pair of mating luer connectors for selectively joining the reusable and disposable sets, and a check valve downstream of the spike. One large container of contrast media may then be used with multiple patients by switching out the disposable set between patient uses.

Typical contrast dispensing systems include a number of different components such as tubing, valves and luer connectors and the like which represent significant cost both in materials and in terms of labor to assemble the components into the respective reusable and disposable sets. Further, the reservoir has a relatively large diameter compared to the tubing and other components of the system and thus presents the concern that as contrast media enters the reservoir, the entering fluid will free fall onto the top surface of the media in the reservoir creating bubbles. One approach to avoid the formation of such bubbles is to locate a deflector plate below the inlet port of the reservoir so that the fluid will fall into the plate and then be dispersed so as to sheet-off around the periphery of the reservoir adjacent the wall thereof. One drawback to the use of a deflector plate, however, is that the incoming fluid has a tendency to free fall against the plate and splatter. The splatter might be a source of bubbles. Also, where the reservoir is vented, as is typical, the splattering contrast media may interfere with the operation of the vent thus necessitating complex venting structure. Another alternative is to include a downwardly directed, and angled or bent, tube which communicates from the inlet port down into the reservoir and against the wall thereof. Such a bent tube confines the media to avoid splatter, but may have drawbacks of its own. The lube itself may become immersed in the contrast media. Also, all of the incoming contrast media is forced into one location against the reservoir wall.

SUMMARY OF THE INVENTION

The present invention provides an improved contrast dispensing system which overcomes the abovementioned drawbacks. To this end, and in accordance with the principles of the present invention, the reservoir is in the disposable set with the check valve directly attached to the inlet port of the reservoir, and the disposable set mating luer connector attached directly to the check valve. As a consequence, the cost of the tubing that would normally have been therebetween, as well as the additional cost of mounting the components to respective ends of the tubing, is eliminated thereby reducing cost.

In accordance with another aspect of the present invention, the reservoir has a chamber the top of which is integrally molded plastic having an inlet port at the top thereof, and a lateral pipe extending across the underside thereof. The lateral pipe is adjacent to, and advantageously has its upper extent defined by, the underside of the chamber top so as to be held at the top of the chamber away from the bulk of contrast media therein. The lateral pipe has an upper tap communicating with the fluid inlet port and a pair of lower cut-outs at opposite ends of the lateral pipe. The fluid coming into the chamber first passes through the inlet port and directly through the tap so as to be confined within the lateral pipe. The confined media is thereafter dispersed at opposite ends of the pipe into two different locations through the cut-outs. As a consequence, the drawbacks of both the deflector plate and the bent lube are avoided.

The chamber top may further have an integrally formed vent port for venting the chamber. Advantageously, the vent port is out of alignment with the lateral pipe. In accordance with a yet further aspect of the present invention, a flip cap, such as is found on vented spikes, is provided by which to selectively close the vent port. The nip cap may be in the form of a nip cap assembly with a spout and hinged cap, or may be a hinged cap attached directly to the vent port. The flip cap avoids the use of costly or complex venting structures to thereby further minimize cost, for example.

Advantageously, the chamber top is a separate component from the chamber. In this regard, the chamber has an enlarged upper opening and an integrally molded plastic cap member is provided to close that upper opening, with the cap member having the inlet port, lateral pipe and, if provided, the vent port.

By virtue of the foregoing, there is thus provided an improved contrast dispensing system which overcomes certain drawbacks of prior contrast dispensing systems. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

FIG. 2 is a cross-sectional view primarily of the reservoir of the disposable set of the system of FIG. 1, with the reservoir being empty;

FIG. 3 is a view taken along lines 3—3 of FIG. 2 with media in the reservoir;

DETAILED DESCRIPTION OF THE DRAWINGS

Figure 1:
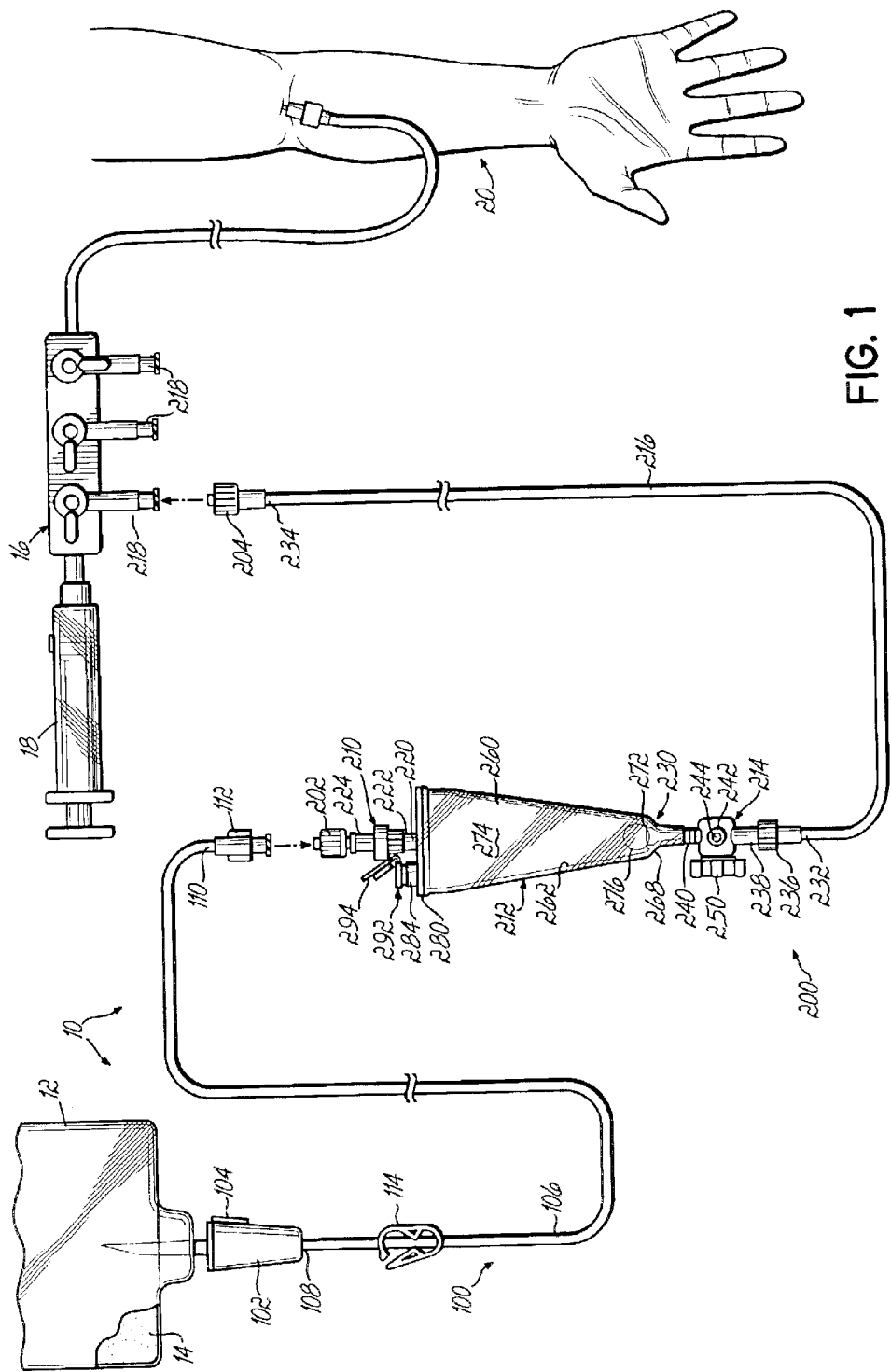
FIG. 1 is an exploded, schematic view, not to scale, of a contrast dispensing system in accordance with the principles of the present invention.

With reference to FIG. 1, there is shown a contrast dispensing system 10 adapted to couple a source 12, such as a bag or bottle, of contrast media 14 to a manifold 16 which, in cooperation with a syringe 18, administers the media 14 to a patient 20. System 10 is comprised of a reusable set 100 and a disposable set 200 which may be selectively coupled together as will be described.

Reusable set 100 includes a spike 102 adapted to be selectively coupled in fluid communication with the media 14 to source 12. Spike 102 may include a hinged vent cap 104, as is typical, for venting of spike 102. Cap 104 is shown in the closed state, but may be flipped open for venting. A length of clear PVC tubing 106 is coupled at one end 108 thereof to spike 102, and at opposite end 110 thereof to a first mating luer connector such as female luer lock 112 for coupling to disposable set 200. Tubing 106 advantageously includes a valve 114 by which to selectively control the flow of fluid through tubing 106 between source 12 and luer connector 112. In the embodiment shown in FIG. 1 the valve 114 is a pinch clamp mounted on tube 106, although other valves may be used such as a stopcock (not shown) inserted in series with the tubing 106. Clamp 114 may either be in an open state as shown in FIG. 1, in which case fluid may flow between spike 102 and connector 112, or may be pinched into the closed state (not shown) in which case tubing 106 is clamped closed to prevent flow of fluid. A vented protector cap (not shown) may also be provided to close off connector 112 when connector 112 is not connected to a second mating luer connector, such as male luer lock 202, of a disposable set 200, for example.

Disposable set 200 is adapted to couple media 14 between connector 202 and the outlet luer connector, such as male luer lock 204, which is adapted to be coupled to one of ports 218 of manifold 16 so as to facilitate dispensing of contrast media 14 to patient 20. Situated between connectors 202 and 204 is a check valve 210, a reservoir 212, an optional venting valve 214, and a second length of clear PVC disposable tubing 216. Reservoir 212 includes an inlet port 220 to which is directly mounted the outlet side 222 of check valve 210, with the inlet side 224 of valve 210 being directly mounted to mating luer connector 202. By directly coupling luer connector 202 to check valve 210, and check valve 210 to inlet port 220 of reservoir 212, there is no need for tubing therebetween thereby minimizing cost and labor associated with that aspect of system 10. Advantageously, inlet port 220, check valve 210, and luer connector 202 are generally permanently secured together such as with adhesive and/or by ultrasonic welding or solvent bonding.

Reservoir 212 further includes a fluid outlet 230 which may be valved as will be described hereinbelow. Tubing 216 has an upper end 232 which is in fluid communication with fluid outlet 230, advantageously via venting valve 214 (although valve 214 could be eliminated), and an opposite, lower end 234 to which is secured outlet luer connector 204. Advantageously, upper end 232 of tubing 216 is secured to a further luer connector 236, such as a male luer lock, which is then secured to the outlet port 238 of valve 214. Valve 214 further has an inlet port 240 secured in fluid outlet 230. Valve 214 may be a three-way stopcock having a third port 242 coupled to atmosphere through a female luer port filter 244 secured therein. Filter 244 may be a 5 micron polypropylene material to filter air entering into valve 214 through port 242. Stopcock 214 further includes a control handle 250 which may be rotated between first and second positions. In the first position of handle 250, fluid outlet 230 communicates directly to tubing 216 through valve 214, with atmosphere port 242 not fluidicly coupled thereto. In the second position of control handle 250, inlet port 240 of valve 214 is cut off, and atmosphere port 242 communicates to outlet port 238 to thereby vent tubing 216 and allow the medical practitioner (not shown) to utilize any contrast media 14 remaining in tube 216 (such as after reservoir 212 has been emptied). Stopcock 214 thus comprises one example of a valve adapted to selectively communicate with atmosphere which is located between reservoir fluid outlet 230 and the first end 232 of disposable tubing 216.

With further reference to FIGS. 2 and 3, it may be seen that reservoir 212 includes a chamber 260 having a wall 262 extending between an enlarged opening 264 at the upper end 266 thereof, and fluid outlet 230 at the lower end 268 thereof. Wall 262 may be cylindrical or rectangular in cross-section, although in the embodiment shown, wall 262 is frustro-conical being tapered between opening 264 and fluid outlet 230. Further, wall 262 may be rigid, although in the embodiment shown, wall 262 is flexible. Chamber 260 may thus be seen as comprising a flexible drip chamber. Fluid outlet 230 may be defined by a fluid outlet port 270 coupled to a valve seat 272 within the interior 274 of chamber 260 defined by wall 262, and a ball seal 276 to thereby provide a valve function to outlet 230. In this regard, ball seal 276 is selected to float in media 14, and to have a diameter to seat in and occlude valve seal 272 when media 14 is drained out of chamber 260 to thereby seal off outlet port 270. Other types of valve arrangements may be provided for outlet 230 (if valuing is desired), such as a sealing disc (not shown) in chamber 260, or a manually operable two-way stopcock (not shown) coupled to port 270, as is conventional.

Figure 4:
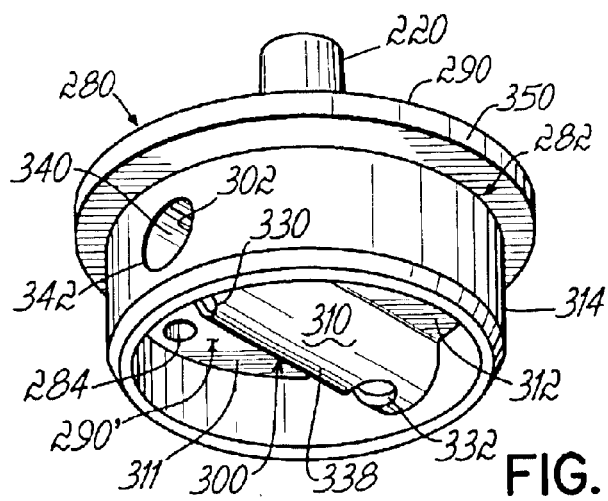
FIG. 4 is a bottom, perspective view of the reservoir cap of FIG. 3.

A cap member 280 closes the opening 264 of chamber 260. Cap member 280 is advantageously an integrally molded plastic member having a peripheral rim 282 (see also FIGS. 3 through 5) engaged with opening 264 and secured thereto (such as with adhesive and/or by ultrasonic welding or solvent bonding). Cap 280 includes a vent port 284 and the fluid inlet port 220, both at the top side 290 of cap 280. Vent port 284 may include mounted thereon a flip cap assembly 292 (generally identical, except for size, to hinged cap 104 on vented spike 102). Assembly 292 includes a spout 293 connected to port 284 and a flip cap 294 connected to spout 293 by one or more hinge strips 295. Vent port 284 may be selectively opened or closed by flip cap 294 simply by flipping it over about hinge strips 295 to close or open spout 293 to thus close or open port 284. To this end, cap 294 includes an engaging lip 296 to frictionally engage with the opening 297 of spout 293 (or vent port 284 if flip cap 294 is hinged directly thereto as may optionally be the case), and a projecting tab 298 to facilitate flipping cap 294 open. Vent port 284 may further include therein a filter 299 so as to provide a filter function between the atmosphere exterior to reservoir 212 and the interior 274 thereof when cap 294 is open to vent reservoir 212.

Figure 5:
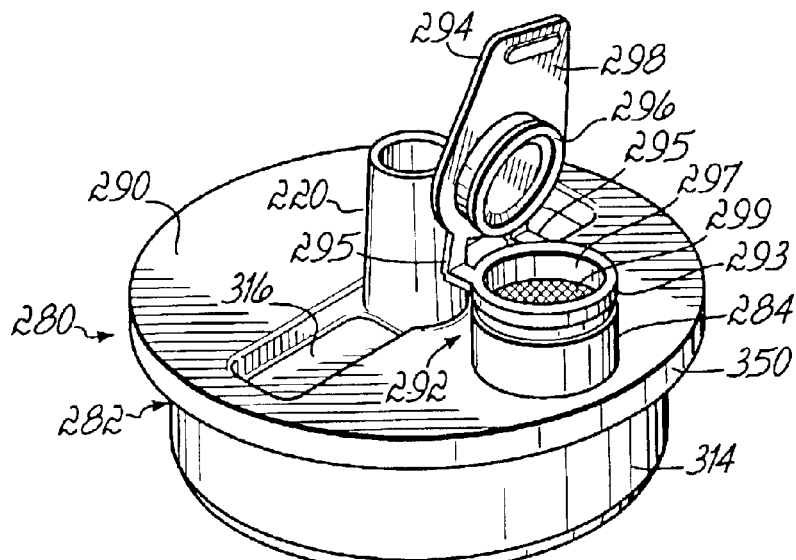
FIG. 5 is a top, perspective view of the cap of FIG. 3.

In order to avoid splatter of media 14 and to disperse same into chamber 260, the underside 290' of cap member 280 includes a lateral pipe 300 extending (horizontally in the Figures) between opposite ends 302, 304. Advantageously, the upper extent 306 of pipe 300 is defined by a portion of the underside 290' of cap 280, with the remaining wall 310 thereof defined by additional plastic during the molding process so as to define recesses 311, 312 to either side of wall 310 within lip 314 of rim 282 below underside 298. The top side 290 may be generally planar as shown in FIG. 5, with a recess 316 defined therein generally coincident with the upper extent 306 of pipe 300.

Figure 6:
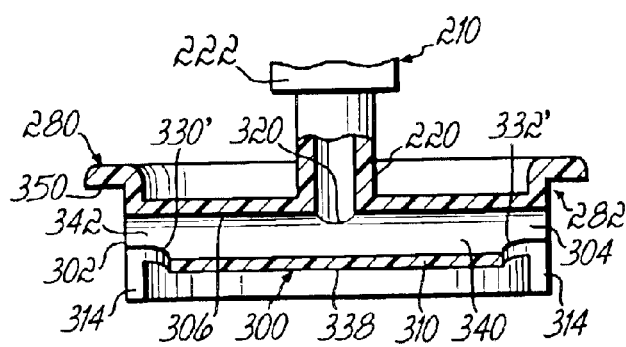
FIG. 6 is a cross-sectional view of an alternative embodiment of a reservoir cap for the disposable set of FIG. 1.

Lateral pipe 300 includes an upper tap 320 which communicates with fluid inlet port 220 so as to receive contrast media 14 and confine same within lateral pipe 300. Formed at the opposite ends 302, 304 of pipe 300 are fluid outlets or cut-outs 330, 332 out of which the contrast media 14 confined within pipe 300 is dispersed so as to exit into the chamber 260 at two separate locations, such as along wall 262 as at 334 and 336, respectively. Cut-outs 330, 332 may be in the form of circular or other shaped openings formed in the lower most extent 338 of plastic wall 310 of lateral pipe 300 so as to be spaced just inwardly of opposite ends 302, 304, or may alternatively be formed directly at ends 302, 304 so as to extend inwardly therefrom as shown in FIG. 6 at 330' and 332'. Vent port 284 is out of alignment, such as by 90°, with lateral pipe 300 to minimize interaction of the media 14 with the vent port 284.

Lateral pipe 300 is shown in the Figures as being a continuous pipe thus having a hollow interior 340 extending between ends 302, 304, although it will be appreciated that lateral pipe 300 could be formed in discrete segments one of which communicates from tap 320 to the cut-out 332 at end 302, and the other of which communicates from tap 320 to the cut-out 334 at end 304. Also, for case of manufacture, at least one of the ends 302, 304 is open as at 342 (see also FIG. 4) with the other end either open or closed as at 344 (FIG. 3). Advantageously, lateral pipe 300 extends so that the opposite ends 302, 304 are adjacent the peripheral rim 282, and advantageously lip 314 thereof. In this way, when cap 280 is received into the opening 264 of chamber 260, the opening(s) 342 becomes sealed off by a segment 346 of the wall 262 of chamber 260 as seen in FIG. 3.

In use, a reusable set 100 and disposable set 200 are joined at mating connectors 112, 202. Spike 102 is coupled to a media source 12, and outlet connector 204 is coupled lo manifold 16. The system 10 is primed and vent port 284 is opened or closed by flip cap 294 as desired for filling, use, or emptying of reservoir 212, and valve 214 manipulated to either couple media 14 from reservoir 212 to manifold 16, or couple tubing 216 to atmosphere for purposes of draining tubing 216, for example. After a patient use, disposable set 200 may be removed at connector 202, and a replacement disposable set 200 may be joined to reusable set 100 and a new manifold 16 for another patient.

By virtue of the foregoing, there is thus provided a contrast dispensing system and/or portions thereof which eliminates the cost of components and labor related to the reservoir inlet and check valve aspects of prior systems, reduces cost and complexity of the venting aspect, and overcomes certain drawbacks of prior reservoir constructions.

While the present invention has been illustrated by the description of embodiments thereof and specific examples, and while the embodiments have been described in considerable detail, it is not intended to restrict or in any way limit the scope of the appended claims to such detail. Additional advantages and modifications will readily appear to those skilled in the art. For example, while the rim 282 is shown as with an annular edge portion 350 and the lip 314 extending down alongside of or below lateral pipe 300, rim 282 could just be the annular edge portion 350 thereof extending about top side 290 of the cap (in which case pipe 300 will be below the rim), or just the lip 314. Tubing 106 and 216 are each shown as single pieces, but each could alternatively be made tip of multiple pieces joined together which would still be considered a length of tubing for purposes herein. Tubing 106 is advantageously about 6 to 10 inches (112–254 mm) in length, and tubing 216 is advantageously about 48 to 72 inches (1219–1830 mm) in length, and advantageously having an inner diameter of about 0.126 inches (3.2 mm) and 0.101 inches (2.6 mm), respectively. The invention in its broader aspects is therefore not limited to the specific details, representative apparatus and methods and illustrative examples shown and described. Accordingly, departures may be made from such details without departing from the scope or spirit of applicant's general inventive concept.

Having described the invention, what is claimed is:

1. A reservoir for a contrast dispensing system comprising:
    a chamber having a wall extending between a large opening at one end of the chamber and a fluid outlet at another end of the chamber, and
    a cap member closing the large opening, the cap being an integrally molded plastic member having a peripheral rim engaged with the chamber opening, a fluid inlet port at a top side of the cap, and a lateral pipe extending between opposite ends thereof adjacent the peripheral rim and across an underside of the cap transverse to the fluid inlet port, the lateral pipe having an upper tap fluidicly coupled to the fluid inlet port, and a pair of lower cutouts at the opposite ends whereby to confine contrast media entering the fluid inlet port in the lateral pipe and to disperse same into the chamber at two separate locations along the wall.

2. The reservoir of claim 1, the chamber wall being tapered.

3. The reservoir of claim 2, the chamber wall being flexible.

4. The reservoir of claim 1, the chamber wall being flexible.

5. The reservoir of claim 1, the chamber including a fluid outlet port and a ball seal and valve seat associated therewith.

6. The reservoir of claim 1, the cutouts being inwardly of the opposite ends of the lateral pipe.

7. The reservoir of claim 1, the cutouts extending inwardly from the opposite ends of the lateral pipe.

8. The reservoir of claim 1, the underside of the cap defining an upper extent of the lateral pipe.

9. The reservoir of claim 1 further comprising a check valve coupled directly to the fluid inlet port of the cap.

10. The reservoir of claim 9 further comprising a luer connector coupled directly to the check valve.

11. The reservoir of claim 10, the luer connector being a male luer lock.

12. The reservoir of claim 1, the lateral pipe having a generally continuous hollow interior between the opposite ends.

13. The reservoir of claim 1, the cap member further having a vent port at the top side of the cap.

14. The reservoir of claim 13, the vent part being out of alignment with the lateral pipe.

15. The reservoir of claim 13 further comprising a flip cap associated with the vent port.

16. The reservoir of claim 1, the fluid outlet being valved.

17. A contrast dispensing system comprising:
a reusable set having a spike adapted to couple to a source of contrast, a first mating luer connector and a length of reusable tubing coupling the spike to the first mating luer connector; and
a disposable set having a second mating luer connector adapted to be removably coupled to the first mating luer connector to selectively join the disposable set to the reusable set, a check valve directly coupled to the second mating luer connector, a reservoir having an inlet port directly coupled to the check valve and further having a fluid outlet, a length of disposable tubing having first and second ends with the first end being in fluid communication with the fluid outlet, and an outlet luer connector in fluid communication with the second end of the disposable tubing and adapted to be coupled to a manifold system for dispensing contrast to a patient.

18. The contrast dispensing system of claim 17, the check valve being generally permanently directly coupled to the second mating luer connector and to the inlet port.

19. The contrast dispensing system of claim 17 further comprising a valve adapted to selectively communicate with atmosphere between the reservoir fluid outlet and the first end of the disposable tubing.

20. The contrast dispensing system of claim 18 further comprising an air filter associated with the valve.

21. The contrast dispensing system of claim 17 further comprising a vent associated with the reservoir.

22. The contrast dispensing system of claim 17, the first and second mating luer connectors being a female luer lock and a male luer lock, respectively.

23. The contrast dispensing system of claim 17, the outlet luer connector being a male luer lock.

24. The contrast dispensing system of claim 17, the fluid outlet being valved.

25. The contrast dispensing system of claim 17, the reservoir including:
a wall extending between a large opening at one end of the chamber and the valved fluid outlet at another end of the chamber; and
a cap member closing the large opening the cap being an integrally molded plastic member with the fluid inlet port at a top side of the cap, and a lateral pipe extending across an underside of the cap transverse to the fluid inlet port, the lateral pipe having an upper tap fluidicly coupled to the fluid inlet port and a pair of lower cutouts at opposite ends of the lateral pipe to confine contrast media entering the fluid inlet port in the lateral pipe and to disperse same into the chamber at two separate locations.

26. The contrast dispensing system of claim 25, the cap having a peripheral rim engaged with the chamber opening, and the opposite ends of the lateral pipe being adjacent the peripheral rim.

27. The contrast dispensing system of claim 25, the lateral pipe having a generally continuous hollow interior between the opposite ends.

28. The contrast dispensing system of claim 25, the cap having a vent port extending at the top side of the cap.

29. The contrast dispensing system of claim 28, the vent port being out of alignment with the lateral pipe.

30. The contrast dispensing system of claim 28 further comprising a flip cap associated with the vent port.

31. A cap for a reservoir of a contrast displeasing system comprising an integrally molded plastic member having a peripheral rim, a fluid inlet port at a top side of the cap, and a lateral pipe extending between opposite ends thereof and across an underside of the cap transverse to the fluid inlet port, the lateral pipe having an upper tap fluidicly coupled to the fluid inlet port and a pair of lower cutouts at opposite ends of the lateral pipe to confine contrast media entering the fluid inlet port in the lateral pipe and to disperse same at two separate locations into a chamber with which the cap is associated.

32. The cap of claim 31 further having a vent port at the top side of the cap.

33. The cap of claim 31, the vent port being out of alignment with the lateral pipe.

34. The cap of claim 31 in combination with a flip cap associated with the vent port.

35. The cap of claim 31, the lateral pipe opposite ends being adjacent the peripheral rim.

36. The cap of claim 31, the lateral pipe having a generally continuous hollow interior between the opposite ends.

37. The cap of claim 31, the cutouts being inwardly of the opposite ends of the lateral pipe.

38. The cap of claim 31, the cutouts extending inwardly from the opposite ends of the lateral pipe.

39. The cap of claim 31, the underside of the cap defining an upper extent of the lateral pipe.

40. The cap of claim 31 in combination with a check valve coupled directly to the fluid inlet port of the cap.

41. The cap of claim 31 in combination with a check valve coupled directly to the fluid inlet port of the cap and a luer connector directly coupled to the check valve.

42. The cap of claim 31 in combination with a check valve coupled directly to the fluid inlet port of the cap and a male luer lock directly coupled to the check valve.

43. A reservoir for a contrast dispensing system comprising a chamber having an integrally molded plastic upper end with a fluid inlet port at a top side thereof, and lateral pipe extending across an underside thereof transverse to the fluid inlet port, the lateral pipe having an upper tap fluidicly coupled to the fluid inlet port, and a pair of lower cutouts at the opposite ends whereby to confine contrast media entering the fluid inlet port in the lateral pipe and to disperse same into the chamber at two separate locations along a wall extending from the upper end.

* * * * *

UNITED STATES PATENT AND TRADEMARK OFFICE
CERTIFICATE OF CORRECTION

PATENT NO. : 6,800,072 B2
DATED : October 5, 2004
INVENTOR(S) : Charles R. Patzer It is certified that error appears in the above-identified patent and that said Letters Patent is hereby corrected as shown below:

Title Page,
Item [57], ABSTRACT,
Line 6, "having the inlet port (200) and a" should read -- having the inlet port (220) and a --

Column 1,
Lines 27-28, "loaded into tile reservoir from the source. The media is then taken from tile reservoir by" should read -- loaded into the reservoir from the source. The media is then taken from the reservoir --
Line 65, "The lube itself may become" should read -- The tube itself may become --

Column 2,
Line 29, "and the bent lube are avoided." should read -- and the bent tube are avoided. --
Lines 35-36, "The nip cap may be in the form of a nip cap" should read -- The flip cap may be in the form of a flip cap --

Column 5,
Line 30, "for case of manufacture," should read -- for ease of manufacture, --
Line 32, "as a 344 (FIG. 3)." should read -- as at 344 (FIG. 3). --
Line 41, "is coupled lo manifold 16." should read -- is coupled to manifold 16. --

Column 6,
Line 5, "could alternatively be made tip of multiple" should read -- could alternatively be made up of multiple --
Line 23, "end of the chamber, and" should read -- end of the chamber; and --
Line 62, "the vent part being out of" should read -- the vent port being out of --

Column 7,
Line 42, "closing the large opening the cap being" should read -- closing the large opening, the cap being --

UNITED STATES PATENT AND TRADEMARK OFFICE
CERTIFICATE OF CORRECTION

PATENT NO. : 6,800,072 B2
DATED : October 5, 2004
INVENTOR(S) : Charles R. Patzer It is certified that error appears in the above-identified patent and that said Letters Patent is hereby corrected as shown below:

Column 8,
Line 10, "reservoir of a contrast displeasing system" should read -- reservoir of a contrast dispensing system --

Signed and Sealed this

Eighth Day of February, 2005

JON W. DUDAS
*Director of the United States Patent and Trademark Office*